| United States Patent [19] | [11] | 4,152,364 |
|---|---|---|
| Chu | [45] | May 1, 1979 |

[54] SELECTIVE PRODUCTION OF PARA-XYLENE

[75] Inventor: Chin-Chiun Chu, North Brunswick, N.J.

[73] Assignee: Mobil Oil Corporation, New York, N.Y.

[21] Appl. No.: 870,958

[22] Filed: Jan. 19, 1978

[51] Int. Cl.² ............................................. C07C 3/52
[52] U.S. Cl. .................................. 585/454; 585/466
[58] Field of Search ...................... 260/671 M, 671 C

[56] References Cited

U.S. PATENT DOCUMENTS 3,965,208  6/1976  Butter et al. .................... 260/671 M

*Primary Examiner*—Delbert E. Gantz
*Assistant Examiner*—C. E. Spresser
*Attorney, Agent, or Firm*—Charles A. Huggett; Ronald J. Cier

[57] ABSTRACT

Process for the selective production of para-xylene by methylation of toluene in the presence of a catalyst comprising a crystalline aluminosilicate zeolite, said zeolite having a silica to alumina ratio of at least about 12 and a constraint index, as hereinafter defined, within the approximate range of 1 to 12, which catalyst has undergone prior modification by treatment with an ammonium hydrogen phosphate to deposit at least about 0.5 weight percent of phosphorus thereon.

10 Claims, No Drawings

SELECTIVE PRODUCTION OF PARA-XYLENE

BACKGROUND OF THE INVENTION

1. Field of the Invention

This invention relates to a process for the selective production of para-xylene by catalytic methylation of toluene in the presence of an ammonium hydrogen phosphate treated crystalline aluminosilicate zeolite catalyst.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of paraxylene over the approximate temperature range of 200° C. to 275° C., with the maximum yield of para-xylene in the mixture of xylenes, i.e., about 50 percent of the xylene product mixture, being observed at 225° C. Higher temperatures were reported to result in an increase in the yield of meta-xylene and a decrease in production of para- and ortho-xylenes.

U.S. Pat. No. 3,965,207 describes methylation of toluene to selectively yield para-xylene at a temperature between about 500° C. and about 750° C. in the presence of a ZSM-5 type zeolite catalyst. U.S. Pat. No. 3,965,208 describes the methylation of toluene, under conditions such that the formation of meta-xylene is suppressed and the formation of ortho- and para-xylene is enhanced, carried out in the presence of a catalyst comprising a crystalline aluminosilicate zeolite of the ZSM-5 type which had been modified by the addition thereof of a small amount of a Group VA element.

While the above noted prior art is considered of interest in connection with the subject matter of the present invention, the methylation process described herein utilizing a catalyst of a crystalline aluminosilicate zeolite having a silica/alumina ratio of at least about 12, a constraint index within the approximate range of 1 to 12 and which has undergone prior modification by treatment with an ammonium hydrogen phosphate to deposit at least about 0.5 weight percent of phosphorus thereon and thereby achieve unexpectedly high selective production of para-xylene has not, insofar as is known, been heretofore described.

Of the xylene isomers, e.g., ortho-, meta and paraxylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene in preference to meta-xylene or ortho-xylene by reaction of toluene with a methylating agent in the presence of a catalyst comprising a crystalline aluminosilicate zeolite, said zeolite having a silica to alumina ratio of at least about 12 and a constraint index of from 1 to 12, which catalyst has undergone prior modification by treatment with an ammonium hydrogen phosphate to deposit at least about 0.5 weight percent of phosphorus thereon.

Compared to a conventional thermodynamic equilibrium xylene mixture in which the para : meta : ortho ratio is approximately 1.2:1, the process described herein affords a xylene product in which the para-xylene content may exceed 90 percent. The improved yield of para-xylene reduces the cost of separation of para-xylene from its isomer which is the most expensive step in the current method employed for producing para-xylene.

The present process comprises methylation of toluene in the presence of a particular ammonium hydrogen phosphate treated crystalline aluminosilicate zeolite catalyst. The catalyst employed is modified by the addition thereto of at least 0.5 percent by weight of phosphorus as a result of such treatment. The content of phosphorus may be as high as about 25 percent by weight.

DESCRIPTION OF SPECIFIC EMBODIMENTS

In accordance with the process of the invention, toluene is brought into contact, under conversion conditions, with a bed comprising particle-form catalyst containing a crystalline aluminosilicate having: a silica to alumina mole ratio of at least 12 and a constraint index within the approximate range of 1 to 12.

The crystalline aluminosilicate zeolite employed herein is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstrom and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the crystalline free space.

The silica to alumina ratio referred to may be determined by conventional analysis. This ratio is meant to represent as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorp normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions although puckered structures exist such as TMA Offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of course sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction, remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes. However, in all instances, at a temperature within the above-specified range of 550° F. to 950° F., the constraint index will have a value for any given zeolite of interest herein with the approximate range of 1 to 12.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35 with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may have used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

Generally, however, the zeolite either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families includes the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The above crystalline aluminosilicate zeolites employed are, in accordance with the present invention, contacted with a solution of an ammonium hydrogen phosphate. The latter may be either an ammonium dihydrogen phosphate $NH_4H_2PO_4$ or preferably a diammonium hydrogen phosphate $(NH_4)_2HPO_4$. A solution of such compound in a suitable solvent inert with respect to the ammonium hydrogen phosphate and the zeolite may be employed. Generally, the solvent is water.

Prior to reacting the zeolite with the ammonium hydrogen phosphate, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 1-5 hours but may be extended up to 24 hours or longer. While heating temperatures above about 500° C. can be employed, they are not necessary. At temperatures of about 1000° C., the crystal structure of the zeolite tends to deteriorate. After heating in air at elevated temperatures, phosphorus is present in oxide form.

The amount of phosphorus incorporated with the zeolite should be at least about 0.5 percent by weight. However, it is preferred that the amount of phosphorus in the zeolite be at least about 2 percent by weight, particularly when the same is combined with a binder, e.g., 35 weight percent of alumina. The amount of phosphorus can be as high as about 25 by weight or more depending on the amount and type of binder present. Preferably, the amount of phosphorus added to the zeolite is between about 1 and about 15 percent by weight.

The amount of phosphorus incorporated with the zeolite by reaction with the ammonium hydrogen phosphate will depend upon several factors. One of these is the reaction time, i.e., the time that the zeolite and the ammonium phosphate are minimized in contact with each other. Generally, such contact time will be between about 0.25 and about 24 hours. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the ammonium hydrogen phosphate, the conditions of drying of the zeolite after reaction of the zeolite with the treating compound, and the amount and type of binder incorporated with the zeolite. Reaction temperature will generally be between about 20° and about 100° C. The concentration of the ammonium hydrogen phosphate in the reaction mixture is usually between about 5 and about 50 weight percent.

Methylation of toluene in the presence of the above described catalyst is effected by contact of the toluene with a methylating agent, preferably methanol, at a temperature between about 250° C. and about 750° C. and preferably between about 400° C. and about 700° C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. The molar ratio of methylating agent to toluene is generally between about 0.05 and about 20. When methanol is employed as the methylating agent a suitable molar ratio of methanol to toluene has been found to be approximately 1-8 moles of methanol per mole of toluene. With the use of other methylating agents, such as methylchloride, methylbromide, dimethylether, methyl carbonate, light olefins or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene or a mixture of para- and ortho-xylene together with comparatively smaller amounts of meta-xylene may be separated by any suitable means, such as by passing the same through a water condenser and subsequently passing the organic phase through a column in which chromatographic separation of the xylene isomers is accomplished.

The process of this invention may be carried out as a batch-type, semi-continuous or continuous operation utilizing a fixed or moving bed catalyst system. A preferred embodiment entails use of a fluidized catalyst zone wherein the reactants, i.e., toluene and methylating agent, are passed concurrently or countercurrently through a moving fluidized bed of the catalyst. The fluidized catalyst after use is conducted to a regeneration zone wherein coke is burned from the catalyst in an oxygen-containing atmosphere, e.g., air, at an elevated temperature, after which the regenerated catalyst is recycled to the conversion zone for further contact with the toluene and methylating agent reactants.

The following examples will serve to illustrate the advantages of the process of the invention without limiting the same.

EXAMPLE 1

HZSM-5 extrudate, containing 35 percent alumina binder, in an amount of 6 grams was added to a solution of 5 grams of diammonium hydrogen phosphate [$(NH_4)_2HPO_4$] in 10 mls. of water at about 90° C. for 2 hours. After filtration and drying, the residue was calcined at 500° C. for 2 hours to yield a zeolite product containing 7.3 weight percent phosphorus.

EXAMPLE 2

To a 5 gram sample of the phosphorus-containing ZSM-5 catalyst prepared as in Example 1, maintained at the desired temperature, was passed through a mixture of toluene/methanol in a 4:1 molar ratio at a weight hourly space velocity of 10. The results obtained under varying temperature conditions are shown below:

| Temperature ° C. | Percent Toluene Conversion | Percent Para-Xylene in Xylenes |
|---|---|---|
| 300 | 3.4 | 93.0 |
| 350 | 5.6 | 91.7 |
| 400 | 9.9 | 90.2 |
| 450 | 13.5 | 83.2 |
| 500 | 16.0 | 81.0 |
| 550 | 20.0 | 77.5 |
| 600 | 24.0 | 74.8 |

EXAMPLE 3

In a manner similar to that of Example 1, HZSM-5 extrudate having a crystal size of 1-2 microns and containing 35 percent alumina binder in an amount of 6 grams was added to a solution of 4 grams of phosphoric acid ($H_3PO_4$) in 10 ml. of water at about 90° C. for 2 hours. After filtering, drying and calcining at 500° C. for 2 hours, the resultant zeolite product, upon analysis, was found to contain 7.2 weight percent phosphorus.

EXAMPLE 4

To a 5 gram sample of the phosphorus-containing ZSM-5 catalyst prepared as in Example 3, maintained at the desired temperaure, was passed through a mixture of toluene/methanol in a 4:1 molar ratio at a weight hourly space velocity of 10 as described in Example 2. The results obtained under varying temperature conditions are shown below.

| Temperature °C. | Percent Toluene Conversion | Percent Para-Xylene In Xylenes |
|---|---|---|
| 300 | 4.0 | 75.8 |
| 350 | 7.0 | 72.9 |
| 400 | 9.8 | 59.0 |
| 450 | 13.0 | 47.6 |
| 500 | 16.7 | 44.7 |
| 550 | 23.0 | 42.1 |

It will be seen from a comparison of the results of Examples 2 and 4 that the phosphorus-containing ZSM-5 catalyst which had been modified by treatment with diammonium hydrogen phosphate provided substantially higher para-xylene selectivity than the corresponding catalyst which had been modified with phosphoric acid at about the same conversion and approximately the same phosphorus content.

EXAMPLE 5

HZSM-5 extrudate containing 35% alumina binder was added to a solution of 4.5 grams of $NH_4H_2PO_4$ in 10 ml. water at 90° C. and maintained at 90° C. for 2 hours. After filtration and drying, the residue was calcined at 500° C. for 2 hours to yield a zeolite product containing 10.3 weight percent phosphorus.

EXAMPLE 6

To a 5 gram sample of phosphorus-containing ZSM-5 catalyst, prepared as in Example 5, maintained at the desired temperature, was passed through a mixture of toluene/methanol in a 4:1 molar ratio at a weight hourly space velocity of 10 as described in Example 2. The results obtained under varying temperature conditions are shown below:

| Temperature °C. | Percent Toluene Conversion | Percent Para-Xylene in Xylenes |
|---|---|---|
| 350 | 5.3 | 72.7 |
| 400 | 8.7 | 79.5 |
| 450 | 10.3 | 77.9 |
| 500 | 12.7 | 74.3 |
| 550 | 15.4 | 71.7 |
| 600 | 17.9 | 70.8 |

It will be evident from the above results that the phosphorus-containing ZSM-5 catalyst which had been modified by treatment with ammonium dihydrogen phosphate provided selective production of paraxylenes.

It is to be understood that the foregoing description is merely illustrative of preferred embodiments of the invention of which many variations may be made by those skilled in the art within the scope of the following claims without departing from the spirit thereof.

What is claimed is:

1. A process for the selective production of para-xylene which comprises reacting toluene with a methylating agent under methylation conditions in the presence of a catalyst comprising a crystalline aluminosilicate zeolite, said zeolite having a silica to alumina ratio of at least about 12, a constraint index within the approximate range of 1 to 12, said catalyst having undergone prior modification by treatment with an ammonium hydrogen phosphate to deposit at least about 0.5 weight percent of phosphorus thereon.

2. The process of claim 1 wherein said methylating agent is methanol, methyl chloride, methyl bromide, dimethylether or dimethylsulfide.

3. The process of claim 1 wherein said ammonium hydrogen phosphate is diammonium hydrogen phosphate.

4. The process of claim 1 wherein said ammonium hydrogen phosphate is ammonium dihydrogen phosphate 5. The process of claim 1 wherein said crystalline aluminosilicate is ZSM-5.

6. The process of claim 1 wherein said methylation conditions include a temperature between about 250° C. and about 750° C., a pressure within the approximate range of 1 atmosphere to 1000 psig, a weight hourly space velocity between about 1 and about 2000 and a molar ratio of methylating agent to toluene between about 0.05 and about 20.

7. The process of claim 6 wherein said temperature is between about 400° C. and about 700° C.

8. The process of claim 1 wherein said phosphorus is present in an amount of between about 0.5 and about 25 weight percent.

9. The process of claim 1 wherein said crystalline aluminosilicate zeolite is characterized by a silica/alumina ratio in excess of 30.

10. The process of claim 1 wherein said methylating agent is methanol.

* * * * *

UNITED STATES PATENT AND TRADEMARK OFFICE
CERTIFICATE OF CORRECTION

PATENT NO. : 4,152,364
DATED : May 1, 1979
INVENTOR(S) : CHIN-CHIUN CHU

It is certified that error appears in the above-identified patent and that said Letters Patent are hereby corrected as shown below:

Column 2, line 19          "1.2:1 should be -- 1:2:1 --

Column 3, line 59          "fraction," should be -- fraction --

Signed and Sealed this

Thirteenth Day of November 1979

[SEAL]

Attest:

RUTH C. MASON
Attesting Officer

LUTRELLE F. PARKER
Acting Commissioner of Patents and Trademarks